{ United States Patent (12) Matsuo et al.

(10) Patent No.: US 7,430,894 B2
(45) Date of Patent: Oct. 7, 2008

(54) GAS SENSOR

(75) Inventors: Kouji Matsuo, Nagoya (JP); Kazuro Tokushige, Nagoya (JP)

(73) Assignee: NGK Spark Plug Co., Ltd., Aichi-Ken (JP)

(*) Notice: Subject to any disclaimer, the term of this patent is extended or adjusted under 35 U.S.C. 154(b) by 380 days.

(21) Appl. No.: 10/573,855

(22) PCT Filed: Sep. 28, 2004

(86) PCT No.: PCT/JP2004/014152

§ 371 (c)(1),
(2), (4) Date: Mar. 29, 2006

(87) PCT Pub. No.: WO2005/031334

PCT Pub. Date: Apr. 7, 2005

(65) Prior Publication Data

US 2007/0119235 A1 May 31, 2007

(30) Foreign Application Priority Data

Sep. 29, 2003 (JP) ............................ 2003-338887

(51) Int. Cl.
G01N 7/00 (2006.01)
(52) U.S. Cl. .................................... 73/31.05
(58) Field of Classification Search .................. 73/31.05
See application file for complete search history.

(56) References Cited

FOREIGN PATENT DOCUMENTS

| JP | 58-156845 | A | 9/1983 |
|----|-----------|---|--------|
| JP | 5-94759   | U | 12/1993 |
| JP | 6-12527   |   | 3/1994 |
| JP | 8-68776   | A | 3/1996 |
| JP | 2001-133431 | A | 5/2001 |
| JP | 2001-147213 | A | 5/2001 |
| JP | 2001-153833 | A | 6/2001 |
| JP | 2001-311713 | A | 11/2001 |
| JP | 2002-181761 |   | 6/2002 |
| JP | 2003-43003 | A | 2/2003 |

*Primary Examiner*—Hezron E. Williams
*Assistant Examiner*—Rodney T Frank
(74) *Attorney, Agent, or Firm*—Sughrue Mion, PLLC

(57) ABSTRACT

A gas sensor where breakage of a separator can be prevented even if impact is applied to an outer sleeve from outside and the separator can be stably held in the outer sleeve. A separator (82) is received in an outer sleeve (44) without contact with the inner circumferential surface of the outer sleeve (44), and the separator (82) is held in contact with a front end surface (52) of an elastic seal member (50) and urged toward the rear end. At that time, the separator (82) is held between the urging metal piece (200) and the elastic seal member (50) while being urged toward the elastic seal member (50). The urging metal piece (200) is located around a front-end-side portion (301) of the separator (82) and, with effect of a deformed portion (205) of the outer sleeve (44), the urging metal piece (200) is deformed so as to urge the separator (82) toward the rear end. Because of the above structure, even when impact is applied to the outer sleeve (44) from outside, the impact is not directly transmitted to the separator (82) and the elastic seal member (50) absorbs or cushions the impact. As a result, breakage of the separator (82) can be prevented.

6 Claims, 5 Drawing Sheets

GAS SENSOR

TECHNICAL FIELD

The present invention relates to a gas sensor including a sensor element having a plate shape or closed-bottomed tubular shape, which is assembled in a metallic shell or the like, and more particularly to a gas sensor for detecting specific gas components in gas which is an object for measurement by an oxygen sensor, wide-range air-fuel ratio sensor, NOx sensor, or the like.

BACKGROUND ART

As for internal combustion engines, there is conventionally known that combustion control based on detected information on oxygen concentration, etc. in exhaust gas which is a measuring object is effective for energy saving, emission gas purification, and others. As gas sensors for detecting the oxygen concentration, etc. in the exhaust gas, there is known a gas sensor using a sensor element constituted of solid electrolyte such as partially stabilized zirconia. Such gas sensor has variously been improved.

A known one of the above gas sensors has a concrete structure including a sensor element having a gas contact portion which will be exposed to exhaust gas, a metallic shell holding the sensor element, an outer sleeve connected at its front end with the metallic shell, a plurality of electrode output terminals electrically connected to the sensor element, a plurality of lead wires connected one each to the electrode output terminals, a separator accommodated in the outer sleeve and internally setting each electrode output terminal while insulating them from one another, and an elastic seal member formed with insertion holes through each of which each lead wire is inserted. The separator in such gas sensor includes a body part which holds a part of each lead wire and an electrode output terminal, and a flange portion of a larger diameter than that of the body part. The outer sleeve includes a small diameter portion having an inner diameter larger than the outer diameter of the body part and smaller than the outer diameter of the flange part, a large diameter portion having an inner diameter larger than the outer diameter of the flange part, and a shoulder portion connecting the small diameter portion and the large diameter part.

The separator is placed so that one surface of the flange portion engages the shoulder portion of the outer sleeve while the other surface of the flange portion is pressed and fixed by an elastic member (an urging member) fitted under pressure in the large diameter part of the outer sleeve. Thus, the separator is held in the outer sleeve. In short, the separator is fixed between the elastic member and the shoulder portion of the outer sleeve (see Patent Documents 1 and 2, for example).

[Patent Document 1] JP Published patent application No. 2001-147213

[Patent Document 2] JP Published patent application No. 2001-311713

DISCLOSURE OF INVENTION

However, each of the gas sensors disclosed in Patent Documents 1 and 2 is structured such that the separator is fixed between the elastic member and the shoulder portion of the outer sleeve while the flange portion of the separator is in contact with the shoulder portion of the outer sleeve. In case a scattering stone or the like collides against an outer surface of the outer sleeve at a portion contacting with one surface of the flange part, compressive stress resulting from the collision would be transmitted directly to the separator. Consequently, the gas sensors disclosed in Patent Documents 1 and 2 have a problem with that the separator is likely to be damaged when a scattering stone or the like collides against the outer sleeve.

For the gas sensor using the plate shaped sensor element, it is often adopt a structure that the electrode terminal portion is fixedly held between the sensor element and the separator. When the separator is in contact with the outer sleeve, therefore, compressive stress resulting from the collision would be transmitted directly to the separator in case a scattering stone or the like collides against the outer surface of the outer sleeve. This may cause not only damage to the separator but also breakage of the sensor element.

The present invention has been made to solve the above problems and has a purpose to provide a gas sensor adapted to prevent breakage of a separator even when impact is applied to an outer sleeve from outside and to stably hold the separator in the outer sleeve.

To achieve the above purpose, a gas sensor according to claim 1 comprises: a sensor element formed extending in an axial direction and being to be exposed at a front end side to gas which is a measuring object; a metallic shell holding the sensor element; an outer sleeve connected, at its front end portion, with the metallic shell; a plurality of electrode output terminals which are in electrically conductive relationship with the sensor element; a plurality of lead wires connected to the electrode output terminals respectively; a separator accommodated in the outer sleeve and setting therein the electrode output terminals individually while insulating them from one another; and an elastic seal member having lead wire insertion holes through which the lead wires are inserted respectively, the elastic seal member being located in the outer sleeve closer to a rear end side than the separator, wherein the separator is held in the outer sleeve so that it is urged toward a rear end while being in contact with a front end surface of the elastic seal member and an outer circumferential surface of the separator is in noncontact with an inner circumferential surface of the outer sleeve.

In the gas sensor according to claim 2, further, in addition to the structure of the invention disclosed in claim 1, the separator includes a rear-end-side portion positioned on the rear end side, a front-end-side portion positioned on a front end side, and a flange portion positioned between the rear-end-side portion and the front-end-side portion, the flange portion being larger in diameter than the rear-end-side portion and the front-end-side portion and including a front-end-side surface that is formed on a side of the front-end-side portion and faces toward the front end side, and the separator is held between the elastic seal member and an urging member while it is urged toward the rear end in contact relation with the front end surface of the elastic seal member by the urging member applying a pressing force on the front-end-side surface of the flange portion toward the front end surface of the elastic seal member.

In the gas sensor according to claim 3, furthermore, in addition to the structure of the invention disclosed in claim 2, the urging member is located on an outer periphery of the front-end-side portion of the separator and urges the separator toward the rear end by a deformed portion having been deformed into inwardly convex shape resulting from radially inward pressing of a portion of the outer sleeve positioned radially outside the urging member.

In the gas sensor according to claim 4, in addition to the structure of the invention disclosed in claim 2 or 3, the sensor element is of a plate shape and has a plurality of electrode terminal portions on a front and back surfaces on the rear end side, the electrode output terminals are fixedly held between the separator and the sensor element while the electrode output terminals are in contact with the corresponding electrode terminal portions of the sensor element, and a contact portion between each electrode output terminal and each electrode terminal portion of the sensor element and a supported portion of the separator by the urging member are positioned in an offset relation to each other in the axial direction of the gas sensor.

Furthermore, in the gas sensor according to claim 5, in addition to the structure of the invention disclosed in any one of claims 1 to 4, the outer circumferential surface of the separator and the inner circumferential surface of the outer sleeve are spaced 0.5 mm or more in a radial direction.

In the gas sensor according to claim 6, in addition to the structure of the invention disclosed in any one of claims 1 to 5, a rear end surface of the separator is formed in a shape recessed radially inwardly from a peripheral edge, and the separator is held in the outer sleeve so that the peripheral edge of the rear end surface is in contact with the front end surface of the elastic seal member.

According to the gas sensor set forth in claim 1, the separator is adapted to internally set each of the plurality of electrode output terminals electrically connected to the sensor element and improve insulation between the electrode output terminals. This separator is accommodated in the outer sleeve closer to a front side end thereof than the elastic seal member formed with the lead wire insertion holes. The separator is held in the outer sleeve so that the outer circumferential surface of the separator is in noncontact with the inner circumferential surface of the outer sleeve. In other words, in the present invention, the separator is accommodated in the outer sleeve with a clearance for the inner circumferential surface of the outer sleeve. This clearance allows release of the compressive stress resulting from impact even when a scattering stone or the like collides against the outer sleeve. Even if such impact is applied to the outer sleeve from outside, accordingly, the impact will not be transmitted directly to the separator. Damage or breakage of the separator can thus be prevented.

Furthermore, according to the gas sensor set forth in claim 1, in the case where the separator is held in the outer sleeve in noncontact with the inner circumferential surface of the outer sleeve as described above, the separator, which is urged toward the rear end, is held in contact with the front end surface of the elastic seal member having the lead wire insertion holes. According to the present invention where the separator is elastically held in contact with the elastic seal member, the elastic member cushions or absorbs impact even if the impact is applied to the outer sleeve from outside, thereby preventing the separator from wobbling in the outer sleeve. Consequently, according to the present invention, the separator can be held stably in the outer sleeve during use of the gas sensor while the separator is also held in noncontact with the inner circumferential surface of the outer sleeve.

As for this gas sensor, the shape of the sensor element need not be limited in particular; for example, may be a closed-bottomed tubular shape or plate shape. For urging the separator, it is possible to adopt any mechanism (an urging member) which urges the separator toward the rear end. For example, an annular metal plate formed at its outer periphery with a gear-shaped protruding claw-like portion may be pressed into the outer sleeve so that the claw-like portion contacts under pressure with the inner circumferential surface of the outer sleeve, thereby urging the separator toward the rear end.

The separator may be of any material which is less deteriorated at a working temperature and has an insulating property. For example, the material may include ceramics such as alumina and silicon nitride, and engineer plastics such as polyether ether ketone (PEEK), polyether ketone (PEK), polyphenylene sulfide (PPS). The insulating seal member may be for example of a heat-resisting rubber material such as fluororubber and silicone rubber.

According to the gas sensor set forth in claim 2, the separator is formed in the above mentioned specific shape, and the urging member is used to provide pressing force (urge) from the front end side surface of the flange portion toward the front end surface of the elastic seal member, thereby urging the separator to the front end surface of the elastic seal member to hold the separator between the elastic member and the urging member. As supported by the urging member, the separator can be held stably inside the outer sleeve.

According to the gas sensor set forth in claim 3, furthermore, the urging member is located on the outer periphery of the front-end-side portion of the separator and deformed along with the deformed portion of the outer sleeve positioned radially outside the urging member, the deformed portion being pressed radially inwardly and deformed to inwardly protrude, thereby urging the separator toward the rear end. Herein, the urging member which urges the separator toward the rear end may be of a configuration that the urging member itself is press-fitted into and held in the outer sleeve as in the prior art but it is hard to say that appropriate pressing of the urging member into between the separator (specifically, the front-end-side portion of the separator) and the outer sleeve is an easy process in assembling of the gas sensor. In the present invention, therefore, the deformed portion inwardly protruding from the outside of the metallic outer sleeve is formed to simultaneously deform the urging member whereby urging the separator toward the rear end. This makes it possible to facilitate urging of the separator with the urging member toward the rear end and stably holding of the separator inside the outer sleeve, achieving the gas sensor at lower costs.

In the gas sensor set forth in claim 4, furthermore, the sensor element used therein is a plate shaped one having the plurality of electrode terminal portions on the front and back surfaces on the rear end side. The electrode output terminals are fixed between the separator and the sensor element while the electrode output terminals are in contact with any one(s) of the electrode terminal portions of the sensor element.

Meanwhile, in the gas sensor of the present invention, the urging member is used to urge the separator toward the rear end so as to hold the separator in contact with the front end surface of the elastic member. In case a scattering stone or the like collides against the outer sleeve, accordingly, the elastic seal member cushions or absorbs the impact. The separator can thus be prevented from wobbling but, depending on the degree of impact, may a little wobble about the supported region thereof by the urging member. If herein the supported region of the separator by the urging member and the contact region between the electrode output terminal and the electrode terminal portion of the sensor element coincide with each other in the axial direction of the gas sensor, stress caused when the separator wobbles about the supported region thereof by the urging member will likely affect the contact region between the electrode output terminal and the electrode terminal portion of the sensor element. This may cause defects such as cracks or breakage of the plate shaped sensor element.

The gas sensor of the present invention, in contrast, is adapted such that the contact region between the electrode output terminal and the electrode terminal portion of the sensor element and the supported region of the separator by the urging member are offset from each other in the axial direction of the gas sensor. Accordingly, even when the separator wobbles about the supported region thereof by the urging member, stress resulting from the separator wobble will unlikely affect the above contact region, thereby effectively preventing the separator from becoming broken or other defects from arising.

Except that the contact region between the electrode output terminal and the electrode terminal portion of the sensor element and the supported region of the separator by the urging members should be arranged at different positions from each other in the axial direction of the gas sensor, no special limitations are imposed on their positional relationship. In view of effectively obtaining the urging force of the urging member to urge the separator toward the rear end, it is preferable that the supported region is positioned backward of the contact region in the axial direction of the gas sensor.

According to the gas sensor set forth in claim 5, the outer circumferential surface of the separator and the inner circumferential surface of the outer sleeve are spaced 0.5 mm or more apart in a radial direction. Thus, the inner circumferential surface of the outer sleeve unlikely touches the outer circumferential surface of the separator even when the outer sleeve itself is deformed by collision of a scattering stone or the like. This makes it possible to further prevent the separator from becoming damaged.

Furthermore, according to the gas sensor set forth in claim 6, the separator is formed with the rear end surface recessed from the peripheral edge toward the radial inside. This "configuration recessed from the peripheral edge toward the radial inside" represents the state where the rear end surface of the separator is recessed spherically, conically, or in pyramid-like form from the peripheral edge toward the central portion. In concrete terms, a configuration that the rear end surface is concave like a spherical or conical shape. In the present invention, such separator is urged toward the rear end and the rear end surface of the separator is held while its peripheral edge is in contact with the front end surface of the elastic seal member. With this structure, even when the elastic member thermally expands during use of the gas sensor, the front end portion of the expanded elastic seal member can be released into the rear end surface of the separator. Consequently, according to the present invention, in addition to the effects of the invention described in any one of claims 1 to 3, it is possible to effectively prevent damages to the elastic seal member due to restriction (pressure) thereon by the separator even when the elastic seal member thermally expands.

EXPLANATION OF REFERENCE NUMERALS

2: Wide-range air-fuel ratio sensor (Gas sensor), 4: Sensor element, 6: Ceramic sleeve, 8: Sensing portion, 10: Lead frame (Electrode output terminal), 11: First lead frame, 30, 31, 32, 34, 36: Electrode terminal portion, 44: Outer sleeve, 50: Elastic seal member, 54: First tubular portion, 56: Second tubular portion, 58: Third tubular portion, 61: Lead wire insertion hole, 46: Lead wire, 65: Deformed portion, 82: Separator, 83: Flange portion, 86: First frame positioning groove, 88: Second frame positioning groove, 102: Metallic shell, 200: Urging metal piece (Urging member), 211: Second lead frame.

BEST MODE FOR CARRYING OUT THE INVENTION

A description of a preferred embodiment of the present invention will now be given referring to the accompanying drawings.

The present embodiment will be explained about one type of gas sensor; a wide-range air-fuel ratio sensor 2 (hereinafter referred to as an "air-fuel ratio sensor 2") which is mounted in an exhaust pipe for an internal combustion engine and in which a sensor element is incorporated to detect specific gas (concretely, oxygen concentration) of exhaust gas which is a measuring object for use in air-fuel ratio feedback control for cars or various types of internal combustion engines.

Figure 1:
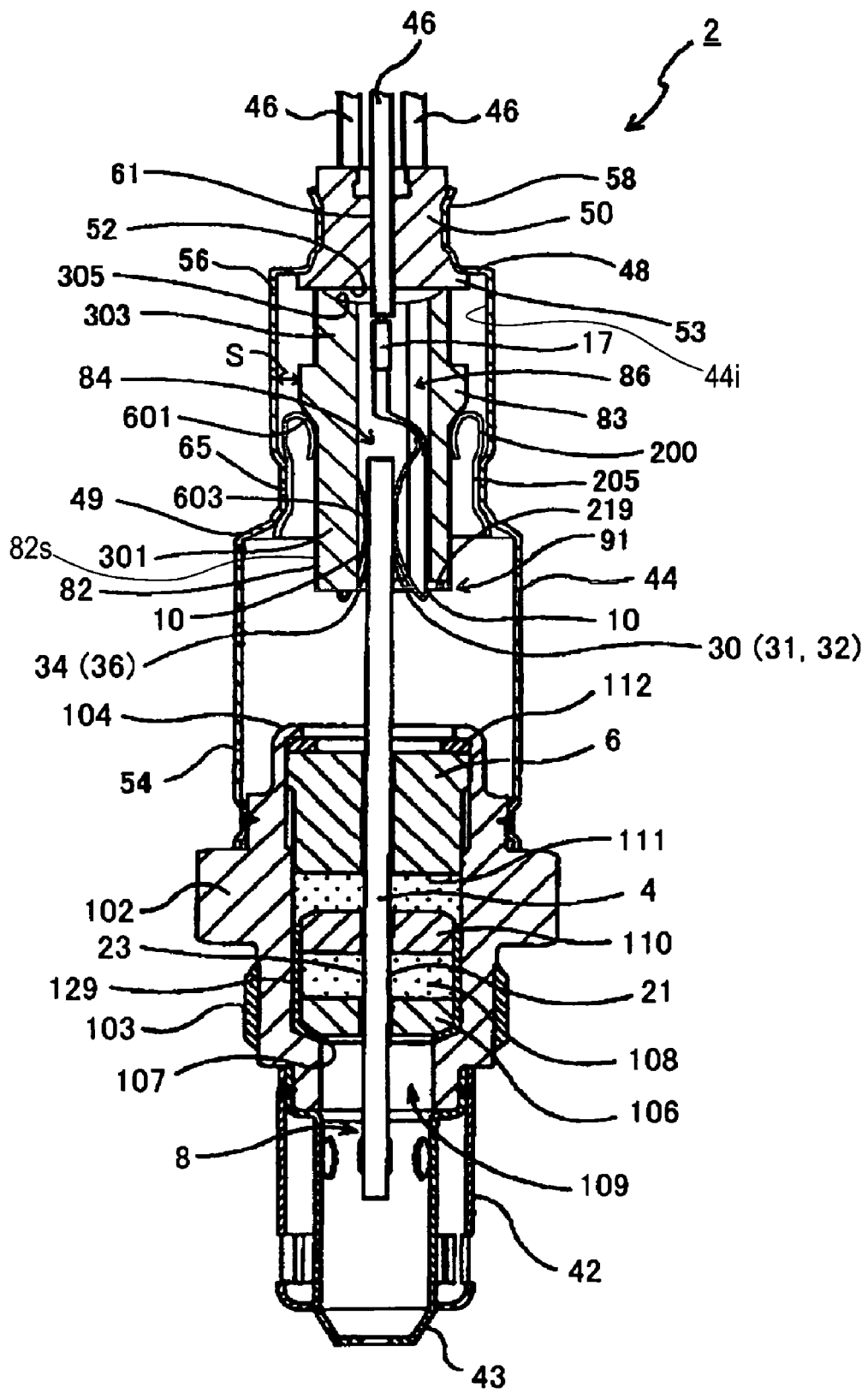
FIG. 1 is a sectional view showing generally a wide-range air-fuel ratio sensor in a preferred embodiment.

FIG. 1 is a sectional view showing the entire structure of the air-fuel ratio sensor 2 in the present embodiment according to the present invention. The air-fuel ratio sensor 2 includes: a tubular metallic shell 102 having an outer surface formed with a threaded portion 103 for fixation to the exhaust pipe; a plate shaped sensor element 4 extending in the axial direction (a vertical direction in the figure); a tubular ceramic sleeve 6 disposed radially surrounding the outer periphery of the sensor element 4; lead frames 10 electrically connected to electrode terminal portions 30, 31, 32, 34, and 36 of the sensor element 4, forming current paths; a separator 82 made of an insulating material and holding the lead frames 10 connected to the electrode terminal portions 30, 31, 32, 34, and 36 of the sensor element 4, between the separator 82 and the sensor element 4; and lead wires 46 forming current paths between the lead frames 10 and the outside of the sensor. Each of the lead wires 46 is constituted of electrically conductive core wires and a resinous insulating coating material covering the core wires, and a front end portion and a rear end portion of the core wires are uncovered with the resinous coating material.

The sensor element 4 is of a plat shape axially extending and is formed with a sensing portion 8 covered with an electrode protecting layer on a front end side (a lower side in the figure) which will be placed for exposure to the gas to be measured and electrode terminal portions 30, 31, 32, 34, and 36 on a first plate surface 21 and a second plate surface 23 forming an outer front and back surfaces on the rear end side (an upper side in the figure). The lead frames 10 are placed between the sensor element 4 and the separator 82, so that the lead frames 10 are electrically connected in contact with the electrode terminal portions 30, 31, 32, 34, and 36 of the sensor element 4 respectively. The lead frames 10 are also electrically and mechanically connected to the lead wires 46 provided extending from outside to inside of the sensor, thereby forming current paths through which electrical currents will pass between an external device (e.g., an ECU) to which the lead wires 46 are connected and the electrode terminal portions 30, 31, 32, 34 and 36.

The metallic shell 102 is designed to be substantially tubular and have a through hole 109 formed axially therethrough and a shoulder 107 protruding radially inwardly in the through hole 109. The metallic shell 102 is also configured to hold the sensor element 4 inserted in the through hole 109 so that the sensing portion 8 is located outside the through hole 9 on the front end side thereof while the electrode terminal portions 30, 31, 32, 34, and 36 are located outside the through hole 9 on the rear end side thereof. The shoulder 107 is formed as a tapered surface inwardly inclined with respect to a flat plane perpendicular to the axial direction.

In the through hole 109 of the metallic shell 102, an annular ceramic holder 106, a powder filled layer 108 (hereinafter, referred to as a talcous ring 108), an auxiliary sleeve 110, a second powder filled layer 111, and the aforementioned ceramic sleeve 6 are placed in layers in this order in a direction from the front to rear end side. Further, a crimping ring 112 is placed between the ceramic sleeve 6 and a rear end portion 104 of the metallic shell 102, and the rear end portion 104 is crimped to press the ceramic sleeve 6 toward the front end side through the crimping ring 112.

A protection cover 129 functioning as a gasket for maintaining air-tightness is placed between the ceramic holder 106 and the shoulder 107 of the metallic shell 102. This protection cover 129 is made of a metal material (e.g., stainless steel) and formed in a tubular shape to cover side surfaces of the ceramic holder 106, talcous ring 108, and auxiliary sleeve 110 and have a bottom portion covering the front-end-side peripheral edge of the ceramic holder 106. The bottom portion of the protection cover 129 has a central opening having a size enough to allow the sensor element 4 to be centrally inserted therein.

Figure 2:
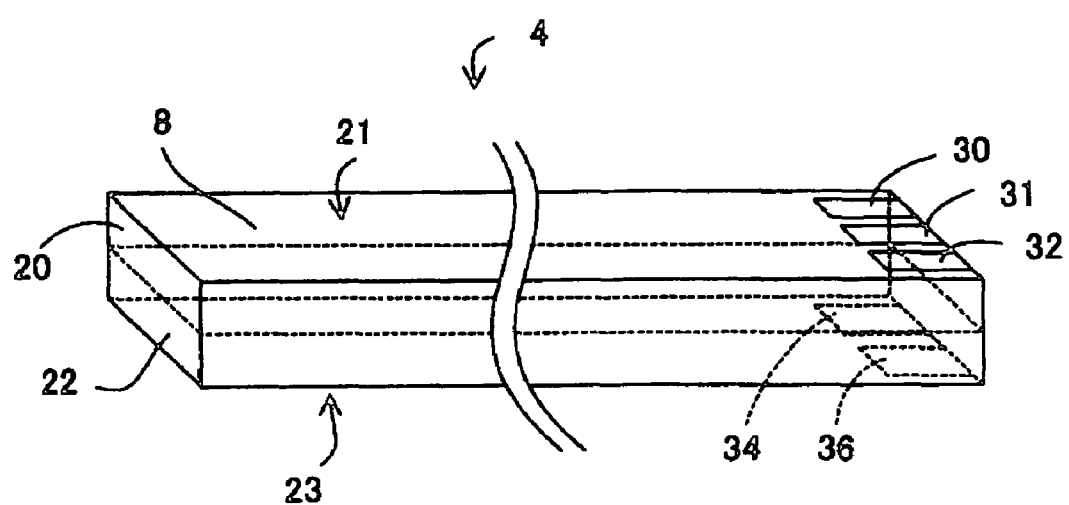
FIG. 2 is a perspective view showing a schematic structure of a sensor element constituting the wide-range air-fuel ratio sensor.

Here, FIG. 2 shows a perspective view showing a schematic structure of the sensor element 4. In FIG. 2, the sensor element 4 is illustrated with its axially middle portion being omitted. The sensor element 4 is formed in a plate shape rectangular in axial section in which a device part 20 formed in a plate shape extending in the axial direction (a right and left direction in FIG. 2) and a heater 22 similarly formed in a plate shape extending in the axial direction are laminated. The sensor element 4 to be used as the air-fuel ratio sensor 2 is a conventionally well known one and therefore the detailed explanation of its internal structure and others is omitted but a schematic structure is as follows.

Firstly, the device part 20 is constituted of an oxygen concentration cell device including a solid electrolyte substrate with porous electrodes provided on both sides thereof, an oxygen pump device identically including a solid electrolyte substrate with porous electrodes provided on both sides thereof, and a spacer layered between those devices and providing a hollow measurement gas chamber. This solid electrolyte substrate is formed of zirconia containing yttria solved as stabilizing agent. The porous electrode is made essentially of Pt. The spacer providing the measurement gas chamber is mainly made of alumina. In the hollow measurement gas chamber, one of the porous electrodes of the oxygen concentration cell device and one of the porous electrodes of the oxygen pump device are exposed. The measurement gas chamber is formed to be positioned at the front end side of the device part 20. In the front end side of the spacer, a diffusion controlled part made of porous ceramic is formed for providing communication between the measurement gas chamber and the outside. This portion including the measurement gas chamber corresponds to the sensing portion 8. The heater 22 is constituted of insulating substrates made essentially of alumina and a heating resistor pattern mainly made of Pt sandwiched between the insulating substrates. The device part 20 and the heater 22 are laminated together through a ceramic layer (for example, zirconia ceramic and alumina ceramic). The sensor element 4 includes, on a surface of at least an electrode of those that are located on the front end side and will be exposed to a measuring object (exhaust gas in the present embodiment), an electrode protecting layer (not shown) made of porous ceramic for preventing poisoning. In the present embodiment, the sensor element 4 on the front end side including the surface of the electrode which will be exposed to exhaust gas is entirely covered with the electrode protecting layer.

In such sensor element 4, as shown in FIG. 2, three electrode terminal portions 30, 31, and 32 are formed on the first plate surface 21 on the rear end side (the right side in FIG. 2) while two electrode terminal portions 34 and 36 are formed on the second plate surface 23 on the rear end side. The electrode terminal portions 30, 31, and 32 are formed on the device part 20; one of which is electrically connected in common to one of the porous electrodes of the oxygen concentration cell device and one of the porous electrodes of the oxygen pump device, both being exposed inside the measurement gas chamber. The remaining two of the electrode terminal portions 30, 31, and 31 are electrically connected to the other porous electrode of the oxygen concentration cell device and the other porous electrode of the oxygen pump device, respectively. The electrode terminal portions 34 and 36 are formed on the heater 22 and connected to both ends of the heating resistor pattern through a via (not shown) intersecting the heater in its thickness direction.

The sensor element 4 structured as above is fixed in the metallic shell 102 in a state as shown in FIG. 1 that the sensing portion 8 arranged on the front end side (the lower side in FIG. 1) protrudes from the front end of the metallic shell 102 which will be fixed to the exhaust pipe and the electrode terminal portions 30, 31, 32, 34, and 36 protrude from the rear end of the metallic shell 102. Further, an external protector 42 and an internal protector 43, each covering the protruded portion of the sensor element 4 and having a plurality of holes and a closed bottom, are welded by laser or the like to the outer periphery of the metallic shell 102 at the front end side (the lower side in FIG. 1), as shown in FIG. 1.

An outer sleeve 44 made of stainless alloy, 0.5 mm in thickness, is fixed to on the outer periphery of the metallic shell 102 on the rear end side thereof. The outer sleeve 44 includes as shown in FIG. 1 a first tubular portion 54 joined to the metallic shell 102, a second tubular portion 56 positioned closer to the rear end than the first tubular portion 54 and having a smaller diameter than the first tubular portion 54, a first shoulder 49 positioned between them, a third tubular portion 58 positioned closer to the rear end than the second tubular portion 56 and having a smaller diameter than the second tubular portion 56, and a second shoulder 48 positioned between them. In the present embodiment, the outer sleeve 44 is fixed to the metallic shell 102 in such a way that the outer sleeve 44 is disposed on the outer periphery of the metallic shell 102 on the rear end side, and an overlapping portion of the outer sleeve 44 with the metallic shell 102 is crimped radially inwardly from outside of the outer sleeve 44 and then is circumferentially weld by laser.

Fitted in a rear end opening of the outer sleeve 44 (i.e., the inside of the third tubular portion 58) is an elastic seal member 50 made of fluororubber, which includes lead wire insertion holes 61 through which five lead wires 46 are inserted and connected to the electrode terminal portions 30, 31, 32, 34, and 36 of the sensor element 4 respectively and a protruding portion 53 protruding radially outwardly.

Furthermore, a separator 82 is located on the rear end side (the upper side in FIG. 1) of the sensor element 4 protruding from the rear end portion 104 of the metallic shell 102. In the present embodiment, this separator 82 is arranged to surround the outer periphery of the sensor element 4 on which the electrode terminal portions 30, 31, 32, 34, and 36 are formed.

Herein, this separator 82 is held inside the surface of 44i of the outer sleeve 44 as shown in FIG. 1 while the outer circumferential surface of the separator 82 is in noncontact with the inner circumferential surface of the outer sleeve 44. To be more concrete, the separator 82 is held inside the outer sleeve 44 while the separator 82 is urged toward the rear end by an urging metal piece 200 mentioned later so that the separator 82 is in contact with a front end surface 52 of the elastic seal member 50 and supported between the front end surface 52 of the elastic seal member 50 and the urging metal piece 200, and also in noncontact with the inner circumferential surface 44i of the outer sleeve 44. In the present embodiment, the outer circumferential surface 82s of the separator 82 and the inner circumferential surface 44i of the outer sleeve 44 are spaced 0.5 mm or more in a radial direction of the air-fuel ratio sensor 2. A minimum distance S between them is set at 1.5 mm.

Figure 4:
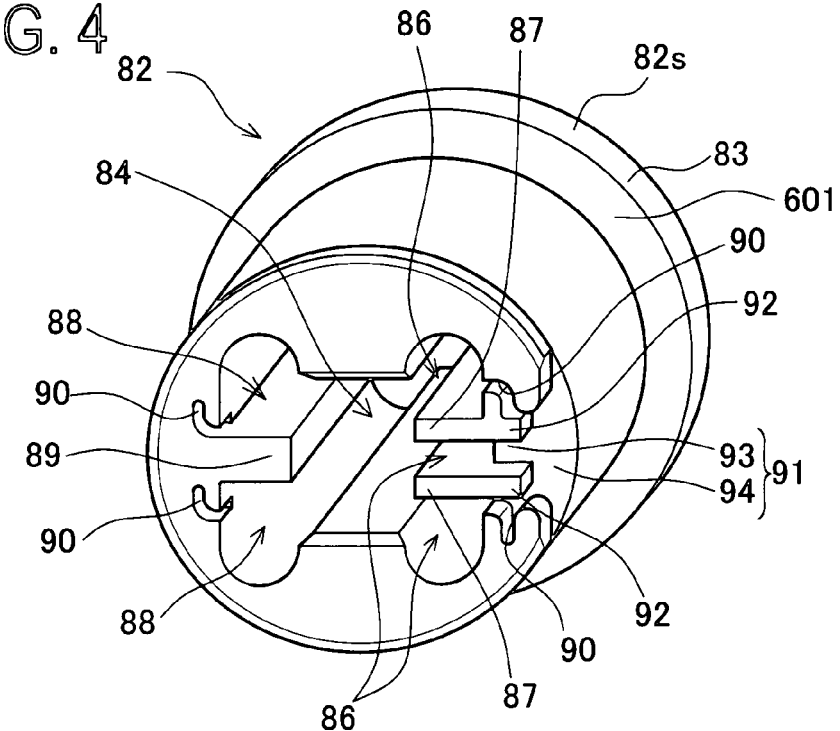
FIG. 4 is a perspective external view of a separator.

The separator 82 will be explained below. FIG. 4 shows a perspective view showing an external view of the separator 82 seen from the front end side. As shown in FIGS. 1 and 4, the separator 82 is formed in a tubular shape having an insertion hole 84 formed axially therethrough and is provided with a rear-end-side portion 303, a front-end-side portion 301, and a flange portion 83 which is interposed between them and of a larger diameter than those of them. As shown in FIG. 1, a rear end surface 305 of the separator 82 (in detail, the rear-end-side portion 303 is formed in a concave shape recessed radially inwardly from the peripheral edge. Specifically, this rear end surface 305 is formed in a spherical shape recessed from the peripheral edge toward the insertion hole 84 centrally positioned.

On an inner wall surface of the insertion hole 84, facing the first plate surface 21 (not shown) of the sensor element 4, two first ribs 87 are formed protruding in an inward direction as shown in FIG. 4. The first ribs 87 are provided as in-insertion-hole lead frame boundary parts forming boundaries between three first frame positioning grooves 86 in which three lead frames 10 are separately arranged in electrically insulated relation. The three first frame positioning grooves 86 are formed at positions corresponding to the electrode terminal portions 30, 31, and 32 on the first plate surface 21 of the sensor element 4.

On an inner wall surface of the insertion hole 84, facing the second plate surface 23 (not shown) of the sensor element 4, a second rib 89 is formed inwardly protruding. The second rib 89 is provided as an in-insertion-hole lead frame boundary part forming a boundary between two second frame positioning grooves 88 in which two lead frames 10 are separately arranged in electrically insulated relation. The two second frame positioning grooves 88 are formed at positions corresponding to the electrode terminal portions 34 and 36 on the second plate surface 23 of the sensor element 4.

The first ribs 87 and second rib 89 have a function for preventing the lead frames 10 arranged in the adjacent frame positioning grooves from contacting each other. Since the lead frames 10 adjacently arranged are prevented from becoming electrically conductive with each other, thus preventing failures of current paths.

The separator 82, on the front end side surface (a forward surface in the figure), includes a first engagement groove 90 and a second engagement groove 91 both being formed opening to the aperture of the insertion hole 84 on the front end side.

The first engagement groove 90 is shaped like generally a letter L as viewed from the front end side of the separator 82 to allow positioning of a first frame engagement portion 19 of the lead frame 10 which will be mentioned later. The first engagement grooves 90 are formed in two places continuing into two of the three first frame positioning grooves 86, provided on both sides, and also in two places continuing into the two second frame positioning grooves 88. The second engagement groove 91 includes a small-width groove portion 93 formed between two protruding portions 92 and a large-width groove portion 94 formed radially outside of the small-width groove portion 93 on the front end side surface of the separator 82 to allow positioning of a second frame engagement portion 219 of the lead frame 10 which will be mentioned later. The protruding portion 92 is shaped to continue from the front end portion of the first rib 87. Further, the second engagement groove 91 is formed in one place continuing into the single first frame positioning groove 86 centrally provided among the three first frame positioning grooves 86.

Figure 6:
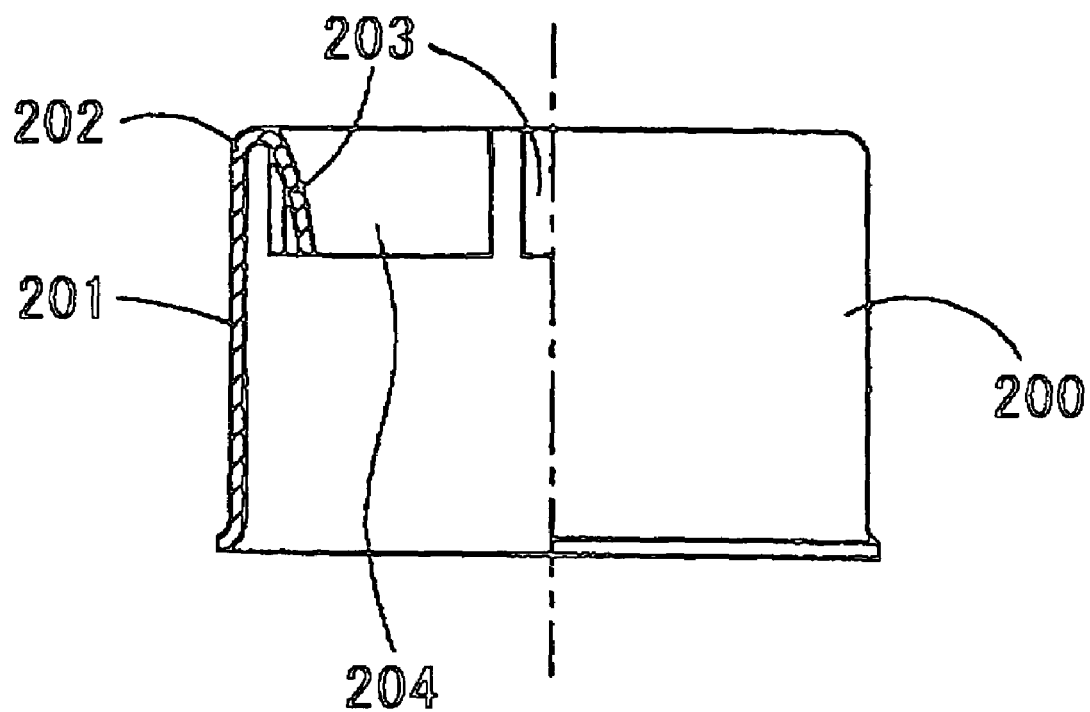
FIG. 6 is a partial cutaway side view of an urging metal piece disposed around the separator at its front-end-side portion.

Subsequently, the urging metal piece 200 will be explained. The urging metal piece 200 is located around the front-end-side portion 301 of the separator 82 as shown in FIG. 1. This urging metal piece 200 has as shown in FIG. 6 a tubular portion 201, and a J-shaped holding portion 203 and a tubular extended portion 204 which are integrally formed with the tubular portion 201 at a rear end 202 thereof. In FIG. 6, the urging metal piece 200 is shown in an earlier state than it is disposed in the outer sleeve 44 and a deformed portion 65 mentioned later is formed. Four J-shaped holding portions 203 are provided at circumferentially equal intervals, extending in a radially inward direction and being gradually turned toward the front end side into generally a letter J. These J-shaped holding portions 203 are configured to be elastically deformed when the urging metal piece 200 is fitted on the separator 82 at the front-end-side portion 301, thereby holding the urging metal piece 200 itself on the front-end-side portion 301. The holding strength can be adjusted depending on the width, shape, and others of the J-shaped holding portions 203.

Each tubular extended portion 204 is formed between the J-shaped holding portions 203 and curved inwardly into a letter J as with the J-shaped holding portions 203. However, the J-shaped holding portions 203 have a curvature adjusted to protrude more inwardly in a radial direction than the tubular extended portions 204. As shown in FIG. 1, at the same time when the deformed portion 65 is formed in the second tubular portion 56 of the outer sleeve, a deformed portion 205 is also formed in the tubular portion 201. Accordingly, the tubular portion 201 urges the front end side surface of the flange portion 83 of the separator 82, that is, the separator 82 toward the rear end.

Figure 3:
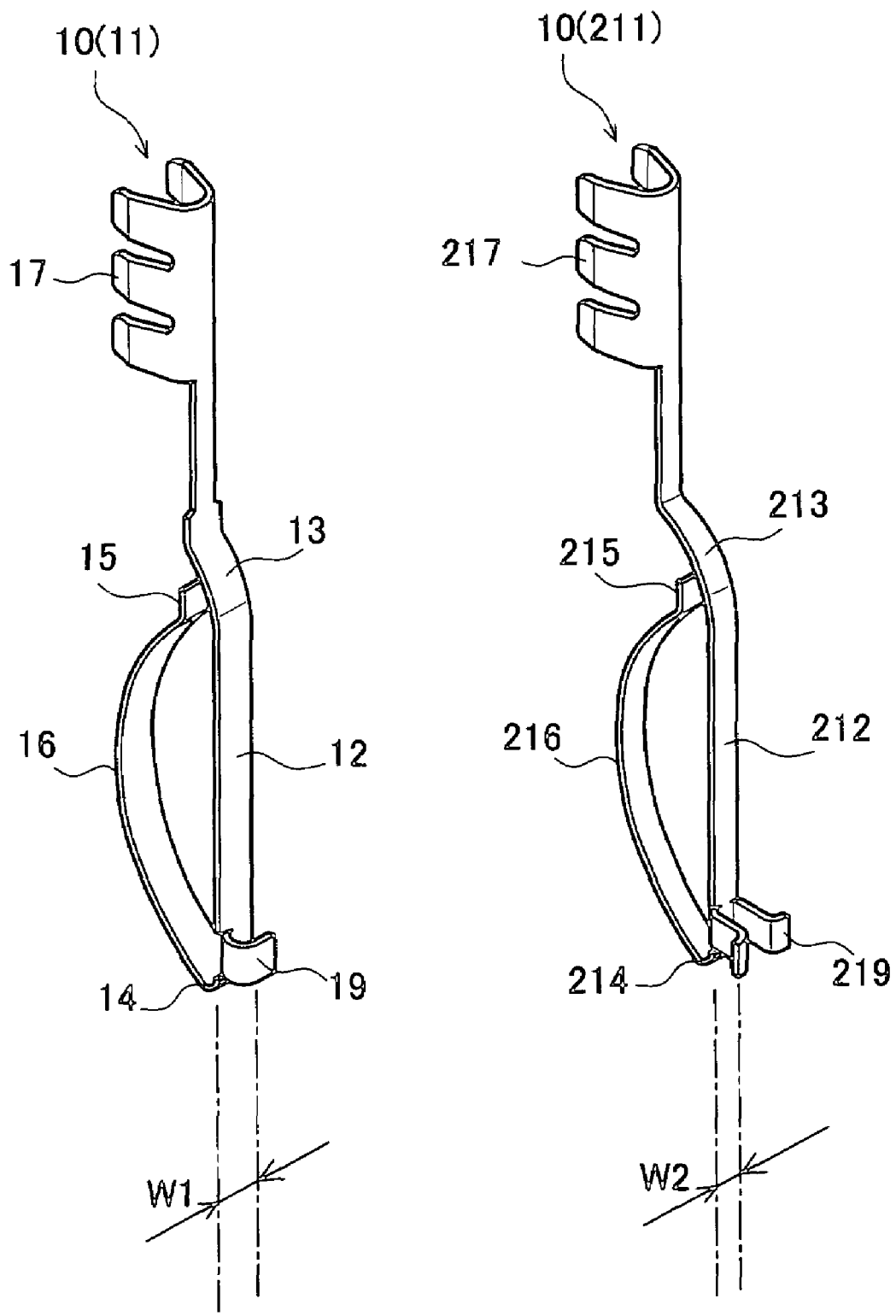
FIG. 3 is a perspective external view of a lead frame.

The lead frames 10 will be explained below. FIG. 3 shows a perspective external view of each lead frame 10. The air-fuel ratio sensor 2 in the present embodiment is designed to include two types of lead frames 10 different in shape of frame engagement part (a first lead frame 11, left one in FIG. 3, and a second lead frame 211, right one). The lead frames 10 are made of a well known material (e.g., inconel, stainless steel) capable of maintaining elasticity (spring resilience) even after it is repeatedly subjected to high temperatures.

Firstly, the first lead frame 11 is constituted of a frame body 12 of a long plat shaped member axially extending and a device contact part 16 extending from the end of the frame body 12 and in a curved shape a part of which is located between the frame body 12 and the sensor element 4, and is arranged to bring the part of the device contact part 16 in contact with one of the electrode terminal portions of the sensor element 4.

The frame body 12 has a curved portion 13 at a substantially midpoint in the axial direction and is designed so that a front end portion positioned closer to the front end than the curved portion 13 and a rear end portion positioned closer to the rear end than the curved portion 13 are placed at different positions in a direction of plate thickness.

The first lead frame 11 is provided, on the front end side of the frame body 12, with the first frame engagement part 19 formed to be placed in the first engagement groove 90 of the separator 82. The first frame engagement part 19 is designed to extend from a side surface of the front end of the frame body 12 toward a direction perpendicular to the plate surface, while being bent to provide a portion parallel to the plate surface of the frame body 12.

The device contact part 16 is formed to have a connected-side end 14 continuous to the front end of the frame body 12 and bent radially inwardly to turn the direction, while an open-side end 15 which becomes a rear end portion in the axial direction is separated from the frame body 12 in a free state of the first lead frame 11 itself. The device contact part 16 is formed in a curved shape so that a clearance distance from the axially midpoint to the frame body 12 is longer than a clearance distance from the open-side end 15 to the frame body 12, and a convex surface of the curved shape is brought into contact with the sensor element 4.

The connected-side end 14 of the device contact part 16 is designed to be elastically deformable on application of external force so that when the connected-side end 14 is elastically deformed, bringing the open-side end 15 closer to the frame body 12, the open-side end 15 comes into contact with the curved part 13 of the frame body 12. This first lead frame is structured such that upon contact of the open-side end 15 with the curved part 13 of the frame body 12, a curved portion of the device contact part 16 is elastically deformed.

Furthermore, the first lead frame 11 includes an integrally formed lead wire connecting part 17 at the rear end of the frame body 12 (the upper end in the figure) and having a larger width than the frame body 12. This lead wire connecting part 17 is formed into a generally tubular shape by bending and then crimped radially inwardly with the core wire of the lead wire 46 (its illustration is omitted) being inserted therein, and thus it is coupled with the lead wire 46.

Next, a second lead frame 211 is constituted of a second frame body 212 having a front portion forward of an intermediate position in the axial direction with a smaller width than the frame body 12 of the first lead frame 11 and a second device contact part 216 with a smaller width than the device contact part 16 of the first lead frame 11.

The second frame body 212 is different in width of the plate surface from the frame body 12 of the first lead frame 11, but is similar to the frame body 12 in sectional shape of a plane parallel to the axial direction and perpendicular to the plate surface, and includes a second curved part 213 corresponding to the curved part 13.

The second device contact part 216 is different in width and thickness of the plate from the device contact part 16 of the first lead frame 11, but is of an arc-shape similar to the device contact part 16 in section of a plane parallel to the axial direction and perpendicular to the plate surface, and includes a second connected-side end 214 corresponding to the connected-side end 14 and a second open-side end 215 corresponding to the open-side end 15.

The second lead frame 211 is provided, on the front end side of the frame body 212, with two frame engagement parts 219 formed to be placed in the second engagement grooves 91 of the separator 82. The second frame engagement parts 219 are designed to extend from the second frame body 212 in a perpendicular direction to the plate surface and be bent outside to form portions parallel to the plate surface of the second frame body 212. The second lead frame 211 further includes, at the rear end of the second frame body 212, a second lead wire connecting part 217 of substantially the same shape as the lead wire connecting part 17 of the first lead frame 11.

Of the lead frames 10 structured as above, four first lead frames 11 and one second lead frame 211 are placed in the insertion hole 84 of the separator 82 while they are insulated from one another by the first ribs 87 and the second rib 89. In this state, the four first lead frames 11 are arranged two in the two first frame positioning grooves 86 corresponding to the electrode terminal portions 30 and 32 of the sensor element 4 and two in the two second frame positioning grooves 88 corresponding to the electrode terminal portions 34 and 36. The second lead frame 211 is arranged in the first frame positioning groove 86 corresponding to the electrode terminal portion 31 of the sensor element 4.

Figure 5:
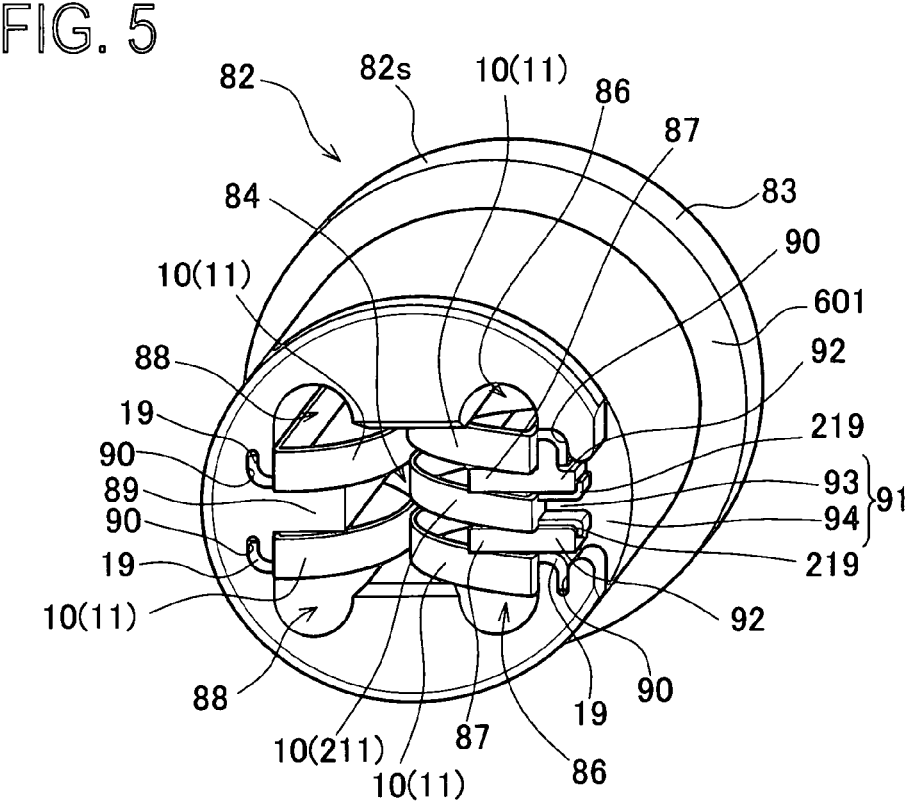
FIG. 5 is a perspective view of the separator wherein the lead frames are placed in an insertion hole.

FIG. 5 shows a perspective view of the separator 82 in which the lead frames 10 are placed in the insertion hole 84. As shown in FIG. 5, when the first lead frame 11 is disposed in the insertion hole 84, the first frame engagement part 19 is engaged in the first engagement groove 90 of the separator 82. When the second lead frame 211 is disposed in the insertion hole 84, the second frame engagement parts 219 of the second lead frame 211 are engaged in the second engagement grooves 91 of the separator 82.

The lead frames 10 are arranged in the insertion hole 84 in such a way that each lead wire connecting part 17 (the second lead wire connecting part 217) is coupled with each lead wire 46 and then the lead frames 10 are inserted together with the lead wires 46 into the insertion hole 84 of the separator 82.

Each lead frame 10 is fixedly held between the inner wall of the insertion hole 84 of the separator 82 and the sensor element 4 while the device contact part 16 is elastically deformed in contact with any one of the electrode terminal portions 30, 31, 32, 24, and 36 of the sensor element 4. In the air-fuel ratio sensor 2 in the present embodiment, as shown in FIG. 1, a contact region 603 between the device contact part 16 of the lead frame 10 and the electrode terminal portion of the sensor element 4 is located forward of a supported region 601 of the separator 82 by the urging metal piece 200, in the axial direction (a vertical direction in FIG. 1) of the air-fuel ratio sensor 2. In the present embodiment, the formation position of the flange portion 83 of the separator 82 is previously adjusted so that the supported region 601 of the separator 82 by the urging metal piece 200 is located backward of the contact region 603 between the device contact part 16 of the lead frame 10 and the electrode terminal portion of the sensor element 4.

A work for assembling the air-fuel ratio sensor 2 while holding the separator 82 assembled with the lead frames 10 in the outer sleeve 44 will be explained below. An assembling method (a manufacturing method) of the air-fuel ratio sensor 2 may include several methods, but two of them are herein exemplified.

A first assembling method of the air-fuel ratio sensor 2 is as follows.

Five lead frames 10 connected one each to the lead wires 46 are disposed in the separator 82 as mentioned above. At this time, the urging metal piece 200 is mounted on the outer periphery of the front-end-side portion 301 of the separator 82 so that the J-shaped holding portion 203 contacts the front-end-side surface 601 of the flange portion 83. Subsequently, the elastic seal member 50 is put on the rear end surface 305 of the separator 82 and in this state the outer sleeve 44 is moved from the elastic seal member 50 side. The outer sleeve 44 is moved until the second shoulder 48 of the outer sleeve 44 comes into contact with the protruding portion 53 of the elastic seal member 50 to house the separator 82 and the elastic seal member 50 in the outer sleeve 44. In this state, the separator 82 is accommodated in noncontact with the inner circumferential surface 44*i* of the outer sleeve 44.

A part of the second tubular portion 56 of the outer sleeve 44, positioned radially outside the tubular portion 201 of the urging metal piece 200, is crimped radially inwardly by use of a pressing jig to form the deformed portion 65, thereby simultaneously deforming the urging metal piece 200 existing inside thereof. Thus, the urging metal piece 200 urges the separator 82 toward the rear end. The deformed portion 65 is formed by round-crimping from all sides. In the case where the urging metal piece 200 is deformed while the separator 82 is held in contact with the front end surface of the elastic seal member 50, the urging metal piece 200 is deformed under a small load (approximately 5N) on the elastic seal member 50 from the rear to front end side to prevent large positional displacement of the elastic seal member 50.

Then, a part of the third tubular portion 58 of the outer sleeve 44, positioned around the elastic seal member 50, is crimped by use of a crimping jig to airtightly seal the elastic seal member 50 with respect to the outer sleeve 44 and each lead wire 46. Accordingly, the separator 82 is fixedly held between the urging metal piece 200 and the elastic seal member 50 and in noncontact with the inner circumferential surface 44*i* of the outer sleeve 44 while the peripheral edge of the rear end surface 305 is in contact with the front end surface 52 of the elastic seal member 50. As just described, an upper assembly is first fabricated.

Then, a work for assembling a lower assembly including the sensor element 4, ceramic sleeve 6, talcous ring 108, ceramic holder 106, metallic shell 102, external protector 42, and others is additionally carried out. This lower assembly is appropriately fabricated so that the rear-end-side portion of the plate shaped sensor element 4 protrudes from the rear end of the metallic shell 102.

The above fabricated upper and lower assemblies are relatively moved to insert the rear end side of the sensor element 4 into the insertion hole 84 of the separator 82 in which the lead frames 10 have been disposed. Accordingly, the device contact portions 16 (the second device contact portion 216) of the lead frames 10 are brought into contact with the electrode terminal portions 30, 31, 32, 34, and 36 of the sensor element 4, providing electrical connection thereto. Then, the outer sleeve 44 (the first tubular portion 54) positioned radially outside the metallic shell 102 is crimped radially inwardly and welded circumferentially by laser to join the outer sleeve 44 to the metallic shell 102. In the above manner, the air-fuel ratio sensor 2 is completed.

Next, a second method for assembling the air-fuel ratio sensor 2 will be explained.

Five lead frames 10 connected one each to the lead wires 46 are disposed in the separator 82 as described above. At this time, the urging metal piece 200 is mounted on the outer periphery of the front-end-side portion 301 of the separator 82 50 that the J-shaped holding portion 203 contacts the front end side surface of the flange portion 83. Subsequently, the elastic seal member 50 is put on the rear end surface 305 of the separator 82 and in this state the outer sleeve 44 is moved from the elastic seal member 50 side. The outer sleeve 44 is moved until the second shoulder 48 of the outer sleeve 44 comes into contact with the protruding portion 53 of the elastic seal member 50 to house the separator 82 and the elastic seal member 50 in the outer sleeve 44. In this state, the separator 82 is accommodated in noncontact with the inner circumferential surface of the outer sleeve 44.

A part of the second tubular portion 56 of the outer sleeve 44, positioned radially outside the tubular portion 201 of the urging metal piece 200, is crimped radially inwardly by use of a pressing jig to form the deformed portion 65, thereby simultaneously deforming the urging metal piece 200 existing inside thereof. Thus, the urging metal piece 200 urges the separator 82 toward the rear end. As just described, an upper assembly is first fabricated. It is to be noted that the deformed portion 65 is formed by round-crimping from all sides. In the case where the urging metal piece 200 is deformed while the separator 82 is held in contact with the front end surface of the elastic seal member 50, the urging metal piece 200 is deformed under a small load (approximately 5N) on the elastic seal member 50 from the rear to front end side to prevent large positional displacement of the elastic seal member 50.

Then, a work for assembling a lower assembly including the sensor element 4, ceramic sleeve 6, talcous ring 108, ceramic holder 106, metallic shell 102, external protector 42, and others is additionally carried out. This lower assembly is appropriately fabricated so that the rear-end-side portion of the plate shaped sensor element 4 protrudes from the rear end of the metallic shell 102.

The above fabricated upper and lower assemblies are relatively moved to insert the rear end side of the sensor element 4 into the insertion hole 84 of the separator 82 in which the lead frames 10 have been disposed. Accordingly, the device contact portions 16 (the second device contact portion 216) of the lead frames 10 are brought into contact with the electrode terminal portions 30, 31, 32, 34, and 36 of the sensor element 4, providing electrical connection thereto.

Herein, in the second assembling method, the separator 82 of the upper assembly is urged toward the elastic seal member 50 in association with the deformation of urging metal piece 200. At that time, however, differently from the aforementioned first assembling method, the elastic seal member 50 is not compressively deformed by crimping to the outer sleeve 44. Accordingly, the separator 82 is held at relatively small holding force between the urging metal piece 200 and the elastic seal member 50. Meanwhile, size tolerances of the ceramic sleeve 6, metallic shell 102, and others and manufacturing factors of the sensor element 4 itself constituting the lower assembly may cause slightly eccentric assembling of the sensor element 4 with respect to the center axis of the metallic shell 102 and warping of the rear-end-side portion protruding from the metallic shell 102.

In the upper assembly in the second assembling method, however, the separator 82 placed between the urging metal piece 200 and the elastic seal member 50 as mentioned above is held at the relatively small holding force. Accordingly, in the case where the rear end of the sensor element 4 is inserted in the insertion hole 84 of the separator 82, the separator 82 is permitted to slightly incline about the supported region 601 of the separator 82 by the urging metal piece 200 even if there is a warp in the rear-end-side portion of the sensor element 4. This makes it possible to effectively prevent the sensor element 4 from becoming cracked or broken.

Then, the outer sleeve 44 (the first tubular portion 54) positioned radially outside the metallic shell 102 is crimped radially inwardly and welded circumferentially by laser to join the outer sleeve 44 to the metallic shell 102. Subsequently, a part of the third tubular portion 58 of the outer sleeve 44, positioned around the elastic seal member 50, is crimped by use of a crimping jig to airtightly seal the elastic seal member 50 with respect to the outer sleeve 44 and each lead wire 46. Accordingly, the separator 82 is fixedly held between the urging metal piece 200 and the elastic seal member 50 and in noncontact with the inner circumferential surface of the outer sleeve 44 while the peripheral edge of the rear end surface 305 is in contact with the front end surface 52 of the elastic seal member 50. In the above manner, the air-fuel ratio sensor 2 is completed.

In the present embodiment, the lead frame 10 corresponds to an electrode output terminal set forth in claims and the urging metal piece 200 corresponds to an urging member.

As described above, in the air-fuel ratio sensor 2 in the present embodiment, the separator 82 is held in the outer sleeve 44 while the outer circumferential surface 82s of the separator 82 is in noncontact with the inner circumferential surface 44i of the outer sleeve 44. In other words, the separator 82 is accommodated in the outer sleeve 44 with a clearance from the inner circumferential surface 44i of the outer sleeve 44. Accordingly, even when a scattering stone or the like collides against the outer sleeve 44, compressive stress resulting from the impact can be released in the clearance. Thus, the impact is not directly transmitted to the separator 82 even where impact is applied from outside of the outer sleeve 44, 50 that breakage of the separator 82 can be prevented.

In the present embodiment, furthermore, in the case where the separator 82 is held in the outer sleeve 44 in noncontact relation with the inner circumferential surface 44i of the outer sleeve 44, the separator 82 is held while being in contact with the front end surface 52 of the elastic seal member 50 and urged toward the rear end. In this way, since the separator 82 is elastically held in contact with the elastic seal member 50, the elastic seal member 50 can cushion or absorb impact even if the impact is applied from outside to the outer sleeve 44, thereby preventing the separator 82 from wobbling in the outer sleeve 44. Consequently, while the separator 82 is held in noncontact relation with the inner circumferential surface of the outer sleeve 44, the separator 82 can be held stably in the outer sleeve 44 during use of the air-fuel ratio sensor 2.

In the present embodiment, furthermore, since the separator 82 is held in the outer sleeve 44 by use of the urging member 200 shown in FIG. 6, the separator 82 can be held stably.

In the present embodiment, the supported region 601 of the separator 82 by the urging metal piece 200 is positioned closer to the rear end in the axial direction of the air-fuel ratio sensor 2 than the contact region 603 between the device contact part 16 of the lead frame 10 and the electrode terminal portion of the sensor element 4. Since the supported region 601 of the separator 82 by the urging metal piece 200 and the contact region 603 between the device contact part 16 of the lead frame 10 and the electrode terminal portion of the sensor element 4 are positioned in an offset relation in the axial direction of the air-fuel ratio sensor 2 as mentioned above, stress resulting from wobble of the separator 82 about the supported region 603 will unlikely affect the contact region 601 and breakage of the sensor element 4 or the like can effectively be prevented from occurring.

Moreover, in the present embodiment, the outer circumferential surface 82s of the separator 82 and the inner circumferential surface 44i of the outer sleeve 44 are spaced 0.5 mm or more as viewed in the radial direction. Therefore the inner circumferential surface 44i of the outer sleeve 44 is unlikely to come into contact with the outer circumferential surface 82s of the separator 82 even when a scattering stone or the like collides against the outer sleeve 44. This makes it possible to effectively prevent breakage of the separator 82.

In the present embodiment, furthermore, the rear end surface 305 of the separator 82 is formed to be spherically recessed from the peripheral edge toward the centrally positioned insertion hole 84 and only the peripheral edge of the rear end surface 305 of the separator 82 is made to contact with the front end surface 52 of the elastic seal member 50. With this structure, it is possible to allow the elastic seal member 50 to be released into the recessed portion of the rear end surface 305 of the separator 82 even when the elastic seal member 50 thermally expands during use of the air-fuel ratio sensor 2. Consequently, even when thermally expands, the elastic seal member 50 can be prevented from becoming damaged due to restriction (pressure) thereon by the separator 82.

The present invention has been explained in the preferred embodiments as above, but it is not limited to the aforementioned embodiments and may be applied with appropriate changes within the scope not departing from the gist thereof. For example, the sensor to which the present invention is applied is not limited to the gas sensor provided with the sensor element formed with five electrode terminal portions and may be applied to any gas sensor including a sensor element having four or less, or, six or more electrodes. Used in the above embodiment is the sensor element constituted of the device part for gas detection and the heater for heating the device part, both being joined through the ceramic layer. Instead thereof, a sensor element constituted of a plate shaped device part and a heater integrally laminated and co-fired.

The invention claimed is:

1. A gas sensor comprising:
   a sensor element formed extending in an axial direction and being to be exposed at a front end side to gas which is a measuring object;
   a metallic shell holding the sensor element;
   an outer sleeve connected, at its front end portion, with the metallic shell;
   a plurality of electrode output terminals which are in electrically conductive relationship with the sensor element;
   a plurality of lead wires connected to the electrode output terminals respectively;
   a separator accommodated in the outer sleeve and setting therein the electrode output terminals individually while insulating them from one another; and
   an elastic seal member having lead wire insertion holes through which the lead wires are inserted respectively, the elastic seal member being located in the outer sleeve closer to a rear end side than the separator,
   wherein the separator is held in the outer sleeve so that it is urged toward a rear end while being in contact with a front end surface of the elastic seal member and an outer circumferential surface of the separator is in noncontact with an inner circumferential surface of the outer sleeve.

2. The gas sensor according to claim 1, wherein
   the separator includes a rear-end-side portion positioned on the rear end side, a front-end-side portion positioned on a front end side, and a flange portion positioned between the rear-end-side portion and the front-end-side portion, the flange portion being larger in diameter than the rear-end-side portion and the front-end-side portion and including a front-end-side surface that is formed on a side of the front-end-side portion and faces toward the front end side, and
   the separator is held between the elastic seal member and an urging member while it is urged toward the rear end in contact relation with the front end surface of the elastic seal member by the urging member applying a pressing force on the front-end-side surface of the flange portion toward the front end surface of the elastic seal member.

3. The gas sensor according to claim 2, wherein
the urging member is located on an outer periphery of the front-end-side portion of the separator and urges the separator toward the rear end by a deformed portion having been deformed into inwardly convex shape resulting from radially inward pressing of a portion of the outer sleeve positioned radially outside the urging member.

4. The gas sensor according to claim 2, wherein
the sensor element is of a plate shape and has a plurality of electrode terminal portions on a front and back surfaces on the rear end side,
the electrode output terminals are fixedly held between the separator and the sensor element while the electrode output terminals are in contact with the corresponding electrode terminal portions of the sensor element, and
a contact portion between each electrode output terminal and each electrode terminal portion of the sensor element and a supported portion of the separator by the urging member are positioned in an offset relation to each other in the axial direction of the gas sensor.

5. The gas sensor according to claim 1, wherein
the outer circumferential surface of the separator and the inner circumferential surface of the outer sleeve are spaced 0.5 mm or more in a radial direction.

6. The gas sensor according to claim 1, wherein
a rear end surface of the separator is formed in a shape recessed radially inwardly from a peripheral edge, and
the separator is held in the outer sleeve so that the peripheral edge of the rear end surface is in contact with the front end surface of the elastic seal member.

\* \* \* \* \*